(12) United States Patent
Yurchenco

(10) Patent No.: US 6,632,790 B1
(45) Date of Patent: Oct. 14, 2003

(54) LAMININ 2 AND METHODS FOR ITS USE

(75) Inventor: Peter Yurchenco, Piscataway, NJ (US)

(73) Assignee: University of Medicine and Dentistry of New Jersey

( * ) Notice: Subject to any disclaimer, the term of this patent is extended or adjusted under 35 U.S.C. 154(b) by 0 days.

(21) Appl. No.: 09/562,702

(22) Filed: Apr. 28, 2000

Related U.S. Application Data

(60) Provisional application No. 60/131,720, filed on Apr. 30, 1999, provisional application No. 60/139,198, filed on Jun. 15, 1999, provisional application No. 60/143,289, filed on Jul. 12, 1999, and provisional application No. 60/155,945, filed on Sep. 24, 1999.

(51) Int. Cl.$^7$ .............................................. C07K 14/00
(52) U.S. Cl. .......................................... 514/2; 530/350
(58) Field of Search ............................... 530/350; 514/2

(56) References Cited

U.S. PATENT DOCUMENTS

| | | |
|---|---|---|
| 5,019,087 A | 5/1991 | Nichols |
| 5,229,365 A | 7/1993 | Potter et al. |
| 5,422,264 A | 6/1995 | Quaranta et al. |
| 5,444,158 A | 8/1995 | Engvall et al. |
| 5,510,263 A | 4/1996 | Quaranta et al. |
| 5,541,106 A | 7/1996 | Jones |
| 5,585,267 A | 12/1996 | Jones et al. |
| 5,624,905 A | 4/1997 | Engvall et al. |
| 5,658,789 A | 8/1997 | Quaranta et al. |
| 5,672,361 A | 9/1997 | Halberstadt et al. |
| 5,681,587 A | 10/1997 | Halberstadt et al. |
| 5,770,562 A | 6/1998 | Burgeson et al. |
| 5,863,743 A | 1/1999 | Campbell et al. |
| 5,872,231 A | 2/1999 | Engvall et al. |

FOREIGN PATENT DOCUMENTS

| | | |
|---|---|---|
| EP | 0204302 | 12/1986 |
| WO | WO 92/12727 | 8/1992 |
| WO | WO 95/08628 | 3/1995 |
| WO | WO 95/09012 | 4/1995 |

OTHER PUBLICATIONS

Pikkarainen et al. 1987; J. Biol. Chem. 262(22):10454–10462.*
Pikkarainen et al. 1988; J. Biol. Chem. 263(14):6751–6758.*
Vachon et al. 1996. J. Cell. Biol. 134(6):1483–1497.*
Vuolteenaho et al. 1990 ; J. Biol. Chem. 265(26):15611–15616.*
Vuolteenaho et al. 1994; J. Cell. Biol. 124(3): 381–394.*
Zhang et al. 1996; J. Biol. Chem. 271(44):27664–27669.*
Utani, et al., *J. Biol. Chem.*, 1995; 270(7): 3292–3298.
Hillier, et al., Database EMEST EBI, Hinxton, U.K., Accession No: AA028205, Aug. 17, 1996.
Agius, E. and Cochard, P., *J. Neurosci.*, 18(1), 1998, pp. 328–338.
Altschul, et al., *J. Mol. Biol.*, 215, 1990, pp. 403–410.
Altschul, et al., *Nucleic Acids. Res.*, 25, 1997, pp. 3389–3402.
Assoain, R. K. and Marcantonio, E. E., *J. Clin. Invest.*, 100(11), 1997, pp. S15–S18.
Aumailley, M. and Kreig, T., J. Invest. Dermatol., 106, 1996, pp. 209–214.
Aumailley et al., *In The Laminins*, Timpl and Ekblom, eds., Harwood Academic Publishers, Amsterdam (1996), pp. 127–158.
Bailey, S. B., et al.,*J. Neurocytology*, 22, 1993, pp. 176–184.
Bates, C. A. and Meyer, R. L., *Dev. Biol.*, 181, 1997, pp. 91–101.
Bernier et al., *Matrix Biol.*, 14, 1995, pp. 447–455.
Bonfil, R. D., et al., *Int. J. Cancer*, 58, 1994, pp. 233–239.
Bowie, J. U. et al., *Science*, 247, 1990, pp. 1306–1310.
Brown, J. C., et al., *J. Cell Sci.*, 107, 1994, pp. 329–338.
Buttery, P. C. and French–Constant, C., *Mol. Cellular Neurosci.*, 14, 1999, pp. 199 212.
Cheng, Y. S., et al., *J. Biol. Chem.*, 272(50), 1997, pp. 31525–31532.
Cleland et al., *Crit. Rev. Therapeutic Drug Carrier Systems*, 10, 1993, pp. 307–377.
Colognato, H., et al,, *J. Cell Biol.*, 145(3), 1999, pp. 619–631.
Colognato, H. and Yurchenco, P. D., *Current Biol.*, 9(22), 1999, pp. 1327–1330.
Cunningham and Wells, *Science*, 244, 1989, pp. 1081–1085.
Dobeli, et al., *J. Biotechnology*, 7, 1988, pp. 199–216.
Donaldson, D. J. and Mahan, J. T., *Cell Tissue Res.*, 235, 1984, pp. 221–224. Ehrig, K., et al., *Proc. Natl. Acad. Sci. USA*, 87, 1990, pp. 3264–3268.
Ehrig, K., et al., *Proc. Natl. Acad. Sci USA*, 87, 1990, pp. 3264–3268.
Engvall et al., *Exp. Cell Res.*, 198, 1992, pp. 115–123.
Ervasti and Campbell, *J. Cell Biol.*, 122(4), 1993, pp. 809–823.
Gayle, et al., *J. Biol. Chem.*, 268, 1993, pp. 22105–22111.
Glukhova, M., et al., *Dev. Biol.*, 157, 1993, pp. 437–447.
Grant, D. S. and Kleinman, H. K., *Regulation of Angiogenesis*, Goldberg I.D., and Rosen, E.M., eds., Birkhauser Verlag, Basel, Switzerland, 1997, pp. 317–333.
Hedin, U., et al., *J. Cell Biol.*, 107, 1988, pp. 307–319.
GenBank entry AA028205.
Kallunki, T., et al.,*J. Cell Biol.*, 266(1), 1991, pp. 221–228.
Kamiguchi, H., et al., *Annu. Rev. Neurosci.*, 21, 1998, pp. 97–125.

(List continued on next page.)

Primary Examiner—Karen Cochrane Carlson
(74) *Attorney, Agent, or Firm*—McDonnell Boehnen Hulbert & Berghoff; David S. Harper

(57) ABSTRACT

The present invention provides substantially purified laminin 2, methods for making recombinant laminin 2, cells that express recombinant laminin 2, and methods for using the substantially purified laminin 2 to accelerate peripheral nervous system nerve regeneration, and to promote cell attachment and migration.

8 Claims, 5 Drawing Sheets

OTHER PUBLICATIONS

Karlin and Altschul, *Proc. Natl. Acad. Sci. USA,* 87, 1990, pp. 2264–2268.
Karlin and Altschul, *Proc. Natl. Acad. Sci. USA,* 90, 1993, pp. 5873–5877.
Kauppila, T. et al., *Exp. Neurol.,* 123, 1993, pp. 181–191.
Kuang, W., et al.,*J. Clin. Invest.,* 102(4), 1998, pp. 844–852.
Lefebvre, O., et al., *Developmental Biol.,* 210, 1999, pp. 135–150.
Leivo and Engvall,*Proc., Natl. Acad. Sci. USA* 85, 1998, pp. 1544–1548.
Malinda, K. M. and Kleinman, H. K., *Int. J. Biochem. Cell Biol.,* 28(9), 1996, pp. 957–959.
Malinda, K. M., et al., *FASEB J.,* 13, 1999, pp. 53–62.
Miner, J. H. and Patton, B. L.,*Int. J. Biochem. Cell Biol.,* 31, 1999, pp. 811–816.
Nicosia, R. F., et al., *Dev. Biol.,* 164, 1994, pp. 197–206.
Nomizu, M., et al., *J. Biol. Chem.,* 272(51), 1997, pp. 32198–32205.
Olsen, D., et al., *Lab. Invest.,* 60(6), 1989, pp. 772–782.
Patton, B. L., et al., *J. Cell Biol.,* 139(6), 1997, pp. 1507–1521.
Patton, B. L., et al., *Neruomusc, Disord.,* 9, 1999, pp. 423–433.
Paulsson, M., et al., *J. Biol. Chem.,* 266(26), 1991, pp. 17545–17551.
Pikkarainen, T., et al., *Eur. J. Biochem.,* 209, 1992, pp. 571–582.
Pinckard et al., *Clin. Exp. Immunol.,* 2, 1967, pp. 331–340.
Ponce, M. L., et al., *Circ. Res.,* 84, 1999, pp. 688–694.
Powell, S. K., et al., *J. Neurosci. Res.,* 54, 1998, pp. 233–247.
Rambukkana, A., et al., *Cell,* 88, 1997, pp. 811–821.
Rambukkana, A., et al., *Science,* 282, 1998, pp. 2076–2078.
Relan, N. K., et al., *J. Cell Biol.,* 147(6), 1999, pp. 1341–1350.
Robbins et al., *Diabetes,* 36, 1987, pp. 838–845.
Ron, et al., *J. Biol. Chem.,* 268, 1993, pp. 2984–2988.
Ryan, M. C. and Christiano, A. M., *Matrix Biol.,* 15, 1996, pp. 369–381.
Sanes et al., *J. Cell Biol.,* 111, 1990, pp. 1685–1699.
Schittney and Yurchenco, *J. Cell Biol.,* 100, 1990, pp. 825–832.
Schreyer, D. J. and Jones, E. G., *Dev. Brain Res.,* 35, 1987, pp. 291–299.
Talts, J. F., et al., *FEBS Lett.,* 426, 1998, pp. 71–76.
Talts, J. F., et al., *EMBO J.,* 18(4), 1999, pp. 863–870.
Talts, J. F. and Timpl, R., *FEBS Lett.,* 458, 1999, pp. 319–323.
Thyberg, J., et al.,*J. Histochem. Cytochem.,* 45(6), 1997, pp. 837–846.
Thyberg, J. and Hultgårdh–Nilsson, A., *Cell Tissue Res.,* 276, 1994, pp. 263–271.
Tisi, D., et al., *EMBO J.,* 19(7), 2000, pp. 1432–1440.
Tong, X. J., et al., *Brain Res.,* 663, 1994, pp. 155–162.
Utani, et al., J. Biol. Chem., 1995; 270(7):3292–3298.
Vilquin, J. T., et al.,*J. Cell Biol.,* 133(1), 1996, pp. 185–197.
Vilquin, J. T., et al., *Gene Therapy,* 6, 1999, pp. 792–800.
Wang, G. Y., et al., *Brain Res.,* 570, 1992, pp. 116–125.
Wewer, U. M. and Engvall, E., *Neuromusc. Disord.,* 6, 1996, pp. 409–418.
White, S. R., et al.,*Am. J. Respir. Cell Mol. Biol.,* 20, 1999, pp. 787–796.
Yurchenco, P. D., et al., *Proc. Natl. Acad. Sci. USA,* 94, 1997, pp. 10189–10194.
Gu, Y., et al., *Blood,* 93(8), 1999, pp. 2533–2542.

\* cited by examiner

FIG. 5

```
5'
+3         R   S   L       K   L   T       K   G   T       A   S   H   W       R   L   I       L   P   R
           TCAGATCCCT      GAAGCTCACC      AAAGGCACAG      CAAGCCACTG      GAGGTTAATT      TTGCCAAGGC
1                         12              21              31              41              51
           AGTCTAGGGA      CTTCGAGTGG      TTTCCGTGTC      GTTCGGTGAC      CTCCAATTAA      AACGGTTCCG
                                                          91                              11

5'
+3         P   W   N   &
                          A
           CCTGGAACTG
61                                      Site of missing base-pair
           GGACCTTGAC
                          T
71
```

LAMININ 2 AND METHODS FOR ITS USE

CROSS REFERENCE

This application claims priority to U.S. Provisional Patent Application Ser. Nos. 60/131,720 filed Apr. 30, 1999; 60/139,198 filed Jun. 15, 1999; and 60/143,289 filed Jul. 12, 1999; 60/155,945 filed Sep. 24, 1999; all of which are incorporated herein by reference in their entirety.

REFERENCE TO GOVERNMENT GRANT

This invention was made with government support under grant R01-DK36425 and R01-AR38454 awarded by the National Institutes of Health. The U.S. government may have certain rights in this invention.

BACKGROUND OF THE INVENTION

Basal laminae (basement membranes) are sheet-like, cell-associated extracellular matrices that play a central role in cell growth, tissue development, and tissue maintenance. They are present in virtually all tissues, and appear in the earliest stages of embryonic development.

Basal laminae are central to a variety of architectural and cell-interactive functions (See for example, Malinda and Kleinman, Int. J. Biochem. Cell Biol. 28:957–959 (1996); Aumailley and Krieg, J. Invest. Dermatology 106:209–214 (1996)). For example:

1. They serve as architectural supports for tissues, providing adhesive substrata for cells.
2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.
3. Basal laminae create highly interactive surfaces that can promote cell migration and cell elongation during embryogenesis and wound repair. Following an injury, they provide a surface upon which cells regenerate to restore normal tissue function.
4. Basal laminae present information encoded in their structure to contacting cells that is important for differentiation and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. To date, six type IV collagen chains and at least twelve laminin subunits have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors, and by forming laminin networks, and they are important signaling molecules that can strongly influence cellular function. Laminins are important in both maintaining cell/tissue phenotype as well as promoting cell growth and differentiation in tissue repair and development.

Laminins are large, multi-domain proteins, with a common structural organization. The laminin molecule integrates various matrix and cell interactive functions into one molecule.

Laminin molecules are comprised of an $\alpha$-, $\beta$-, and $\gamma$-chain subunit joined together through a coiled-coil domain. Within this structure are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. (Kamiguchi et al., Ann. Rev. Neurosci. 21:97–125 (1998)) Domains I and II of the three chains participate in the formation of a triple-stranded coiled-coil structure (the long arm).

Table 1 shows the individual chains that each laminin type is composed of:

TABLE 1

Known laminin family members

| Protein | Chains |
| --- | --- |
| Laminin-1 | $\alpha1\beta1\gamma1$ |
| Laminin-2 | $\alpha2\beta1\gamma1$ |
| Laminin 3 | $\alpha1\beta2\gamma1$ |
| Laminin-4 | $\alpha2\beta2\gamma1$ |
| Laminin-5 | $\alpha3\beta3\gamma2$ |
| Laminin-6 | $\alpha3\beta1\gamma1$ |
| Laminin-7 | $\alpha3\beta2\gamma1$ |
| Laminin-8 | $\alpha4\beta1\gamma1$ |
| Laminin-9 | $\alpha4\beta2\gamma1$ |
| Laminin-10 | $\alpha5\beta1\gamma1$ |
| Laminin-11 | $\alpha5\beta2\gamma1$ |
| Laminin-12 | $\alpha2\beta1\gamma3$ |

Four structurally-defined family groups of laminins have been identified. The first group of five identified laminin molecules all share the $\beta1$ and $\gamma1$ chains, and vary by their $\alpha$-chain composition ($\alpha1$ to $\alpha5$ chain). The second group of five identified laminin molecules all share the $\beta2$ and $\gamma1$ chain, and again vary by their $\alpha$-chain composition. The third group of identified laminin molecules has one identified member, laminin 5, with a chain composition of $\alpha3\beta3\gamma2$. The fourth group of identified laminin molecules has one identified member, laminin 12, with the newly identified $\gamma3$ chain ($\alpha2\beta1\gamma3$)

Some progress has been made in elucidating the relationship between domain structure and function. (See, for example, Wewer and Engvall, Neuromusc. Disord. 6:409–418 (1996).) The overall sequence similarity among the homologous domains in different chains varies, but it is highest in domain VI (thought to play a key role in laminin polymerization), followed by domains V (possibly involved in protein-protein interactions) and III (entactin/nidogen binding; possible cell adhesion sites), and is lowest in domains I, II (both thought to be involved in intermolecular assembly, and containing possible cell adhesion sites), and G. Not all domains are present in all 3 types of chains. The globular G domain (thought to be involved in cell receptor binding) is present only in the $\alpha$ chains. Other domains may not be present in all chains within a certain chain type. For example, domain VI is absent from $\alpha3$, $\alpha4$, and $\gamma2$ chains. (Wewer and Engvall, 1996)

As a result of their large size (>600 kD) and unique structure, laminin molecules can be resolved in the electron microscope. (Wewer and Engvall, 1996) Typically, laminins appear as cross-shaped molecules in an electron micrograph. The three short arms of the cross represent the amino terminal portions of each of the three separate laminin chains (one short arm per chain). The long arm of the cross is composed of the C-terminal parts of the three chains, which together form a coiled coil structure. (Wewer and Engvall, 1996) The long arm ends with the globular G domain.

The coiled-coil domain of the long arm is crucial for assembly of the three chains of laminin. (Yurchenco et al., Proc. Natl. Acad. Sci. 94:10189–10194 (1997)). Disulfide bonds bridge and stabilize all three chains in the most proximal region of the long arm and join the $\beta$ and $\gamma$ chains in the most distal region of the long arm.

A model of laminin receptor-facilitated self-assembly, based on studies conducted with cultured skeletal myotubes and Schwann cells, predicts that laminins bind to their receptors, which freely diffuse in a fluidic membrane when ligand-free. Receptor engagement forces the laminins into a high local two-dimensional concentration, facilitating their mass-action driven assembly into ordered surface polymers. In this process, the engaged receptors are also reorganized, accompanied by cytoskeletal rearrangements. (Colognato, J. Cell Biol. 145:619–631 (1999)) This reorganization activates the receptors, causing signal transduction with the alteration of cell expression, shape and/or behavior.

One class of laminin receptors are the integrins, which are cell surface receptors that mediate many cell-matrix and cell-cell interactions. Integrins are heterodimers, consisting of an $\alpha$ and a $\beta$ subunit. 16$\alpha$- and 8$\beta$-subunits are known, and at least 22 combinations of $\alpha$ and $\beta$ subunits have been identified to date. Some integrins have only one or a few known ligands, whereas others appear to be very promiscuous. Binding to integrins is generally of low affinity, and is dependent on divalent cations. Integrins, activated through binding to their ligands, transduce signals via kinase activation cascades, such as focal adhesion and mitogen-activated kinases. Several different integrins bind different laminin isoforms more or less specifically. (Aumailley et al., In The Laminins, Timpl and Ekblom, eds., Harwood Academic Publishers, Amsterdam. pp. 127–158 (1996))

Laminin 2 is composed of $\beta$2 (400 kD), $\beta$1 (approximately 100 kD), and $\gamma$1 (approximately 100 kD) chains. The C-terminal G domain of the $\beta$2 chain forms a large globular structure responsible for binding to $\alpha$-dystroglycan. (Kamiguchi et al., 1998).

The short arm domains of laminin 1 are involved in the self-aggregation process (Schittney and Yurchenco, J. Cell Biol. 110:825–832 (1990)) and with extracellular matrix components, such as type IV collagen. Homology between the $\alpha$1 (laminin 1) and $\alpha$2 chains is 58.6%. The significant homology between the $\alpha$1 and $\alpha$2 chains, especially in the N-terminal domains, and their identical $\beta$ and $\gamma$ chains, suggest that laminin 2 has a similar structural organization to laminin 1. (Kamiguchi et al., 1998)

Laminin 2 was originally found in the basement membranes of the placenta, striated muscle, and Schwann cells. (Leivo and Engvall, Proc. Natl. Acad. Sci. USA 85:1544–1548 (1998)) In normal adults, laminin 2 is predominant in the basal lamina of skeletal muscle, where it serves to provide mechanical reinforcement to the sarcolemma by linking the extracellular matrix and the subsarcolemmal cytoskeleton. (Sanes et al., J. Cell Biol. 111:1685–1699 (1990)).

Genetic defects affecting the structure or expression of laminin 2 are the causes of a major type of congenital muscular dystrophy (CMD). Laminin 2 has been shown to be specifically required for stabilizing myotubes during skeletal muscle development, and for preventing apoptosis, which is believed to explain some of the pathological events observed in CMD. (Kamiguchi et al., 1998)

In vitro studies have demonstrated that partially purified laminin 2 is important for myotube survival and maintenance of phenotype. (Vachon et al., J. Cell Biol. 134:1483–1497 (1996)). In vivo experiments have shown partial laminin $\alpha$2 chain restoration in a laminin $\alpha$2 deficient, CMD animal model by primary muscle cell transplantation. (Vilquin et al., J. Cell Biol. 133:185–197)

Laminin 2 is also the predominant laminin isoform present in the endoneurial basement membrane of developing and mature peripheral nerves, and was shown to promote Schwann cell migration, neurite outgrowth, and neurite regeneration (Kamiguchi et al., 1998), as well as myelin formation by oligodendrocytes (Buttery et al., Mol. Cell. Neurosci. 14:199–212 (1999). The results of various experiments have indicated that laminin 2, rather than laminin 1, is important in Schwann cell/basal lamina interactions, especially at early developmental stages. (Kamiguchi et al., 1998) Other studies have demonstrated that partially purified laminin 2 promotes neuronal cell migration and axon outgrowth (Agius and Cochard, J. Neurosci. 18:328–338 (1998); Kamiguchi et al, 1998; U.S. Pat. Nos. 5,444,158; 5,872,231; 5,624,905; and 5,863,743; Bates and Meyer, Develop. Biol. 181:91–101 (1997)). In a laminin 2 deficient CMD animal model, CMD was accompanied by dysmyelination of peripheral motor nerves, indicating that laminin 2 plays an important role in peripheral myelinogenesis.

Partially purified laminin 2 has also been shown to promote cell migration and attachment to a substrate of a variety of cell types, particularly muscle cells and cells of neuronal origin. (U.S. Pat. No. 5,444,158; White et al., Am. J. Resp. Biol. 20:787–796 (1999); Engvall et al., Exp. Cell Res. 198:115–123 (1992))

It has also been demonstrated that the molecular basis of the neural tropism of *Mycobacterium leprae* is attributable to the specific binding of *M. leprae* to the G domain of the laminin $\alpha$2 chain on Schwann cell-axon units, while $\alpha$-dystroglycan ($\alpha$DG) was shown to serve as a Schwann cell receptor for *M. leprae*. (Rambukkana et al., Science 282:2076–2079 (1998); Rambukkana et al., Cell 88:811–821 (1997)). Native αDG was shown to competitively inhibit the laminin-2 mediated *M. leprae* binding to primary Schwann cells. (Rambukkana et al. 1998)

Thus, research and therapeutic applications for laminin 2 and fragments thereof include, but are not limited to, peripheral nervous system (PNS) nerve regeneration, treatment of degenerative muscle disorders, regulating angiogenesis, promoting cell attachment and migration, ex vivo cell therapy, improving the biocompatibility of medical devices, improving the "take" of grafts, and preparing improved cell culture devices and media.

At present, there is not a means to isolate adequate substantially purified laminin 2 from cell or tissue sources for research or therapeutic purposes, nor has a means been developed for production of recombinant heterotrimeric laminin 2. Laminin 2 can be partially purified from either placenta, or, in lesser amounts, from skeletal muscle. Human placenta has provided the only source for obtaining up to several milligrams of protein. (Cheng et al., J. Biol. Chem. 272:31525–32, 1997) However preparations of this laminin normally contain about an equal molar quantity of laminin 4 (α2β2γ1) and the protein nidogen (entactin). The nidogen is bound to the laminin through a fairly strong but non-covalent association. It is difficult to remove most of the laminin 4, and even after additional steps, a significant contaminating level of laminin 4 remains. Denaturing conditions are required to remove the nidogen.

Therefore, there is a need in the art for adequate amounts of substantially purified laminin-2, and methods for making laminin 2. A preferred method of production is the use of recombinant DNA technology to engineer a cell line of choice to produce recombinant laminin-2. A recombinant-based method of laminin-2 production has several advantages over purification from tissue or isolation from cell lines in culture:

1. The recombinantly produced protein is free of pathogens. While this is also true for endogenous cell culture produced protein, protein derived from human tissue carries a risk for contamination by HIV, hepatitis, and other infectious agents.
2. Expression levels of the protein, and hence yields, can be improved through the use of genetically engineered genes/vectors that enhance the production of the encoded protein.
3. It is possible to engineer additional peptide sequences to the protein chain that provides a binding site for a commercially viable affinity purification procedure. 4. The method can provide for the modification of protein structure/function through the addition, substitution, elimination, and/or other modifications of protein domain structures. For example, it may be desirable to introduce an integrin binding site (e.g. RGD), switch integrin recognition sites, or engineer in a stable binding site to a synthetic substrate. Thus, the creation of expression vectors that express laminin chains generates enormous flexibility for future uses and creates a basis for creating second generation "designer" laminins.

SUMMARY OF THE INVENTION

The present invention fulfills the need in the art for substantially purified laminin 2 protein, methods for making substantially purified recombinant laminin 2 (hereinafter referred to as r-laminin 2), and methods of using substantially purified laminin 2 for research and therapeutic purposes including, but not limited to, peripheral nerve regeneration, treatment of degenerative muscle disorders, angiogenesis regulation, promoting cell attachment and migration, ex vivo cell therapy, improving the "take" of grafts, improving the biocompatibility of medical devices, and preparing improved cell culture devices and media In one aspect, the present invention provides mammalian cells that have been transfected with expression vector(s) encoding at least one of the laminin α2, β1 and γ1 chains, wherein the cells secrete r-laminin 2.

In another aspect, the present invention provides substantially purified laminin 2 and methods for producing r-laminin 2.

In a further embodiment, the present invention provides a novel, isolated laminin 2 α2 nucleic acid and α2 protein. In this embodiment, the protein product contains an additional 30 amino acids at its carboxyl terminus relative to the previously reported sequence.

In a further aspect, the present invention provides pharmaceutical compositions, comprising substantially purified laminin 2, or the novel recombinant α2 protein together with a pharmaceutically acceptable carrier. Such pharmaceutical compositions can optionally be provided with other compounds, such as extracellular matrix components.

The present invention further provides methods for peripheral nerve regeneration, treatment of degenerative muscle disorders, regulating angiogenesis, promoting cell attachment and migration, ex vivo cell therapy, improving the biocompatibility of medical devices, improving the "take" of grafts, and preparing improved cell culture devices and media, comprising providing an amount effective of the substantially purified laminin 2, or pharmaceutical compositions thereof, for the desired outcome.

In a further aspect, the present invention provides improved medical devices or grafts, wherein the improvement comprises applying to the devices or grafts an amount effective of substantially purified laminin 2 or pharmaceutical compositions thereof, for the desired application. Such devices can optionally be provided with other compounds, such as extracellular matrix components to further improve the biocompatibility or the effectiveness of the medical device or graft.

In a further aspect, the invention provides improved cell culture devices, by providing an amount effective of substantially purified laminin 2, or pharmaceutical compositions thereof, for the attachment of cells to a cell culture device for the subsequent proliferation/differentiation/stasis of the cells.

In another aspect, the invention provides a cell culture growth supplement, comprising substantially purified laminin 2. In another aspect, the invention provides an improved cell culture growth media, wherein the improvement comprises the addition of substantially purified laminin 2 to the growth medium.

BRIEF DESCRIPTION OF THE FIGURES

FIG. 5 shows the correct sequence of the laminin α2 cDNA and deduced amino acid sequence.

DETAILED DESCRIPTION OF THE PREFERRED EMBODIMENTS

Figure 1:
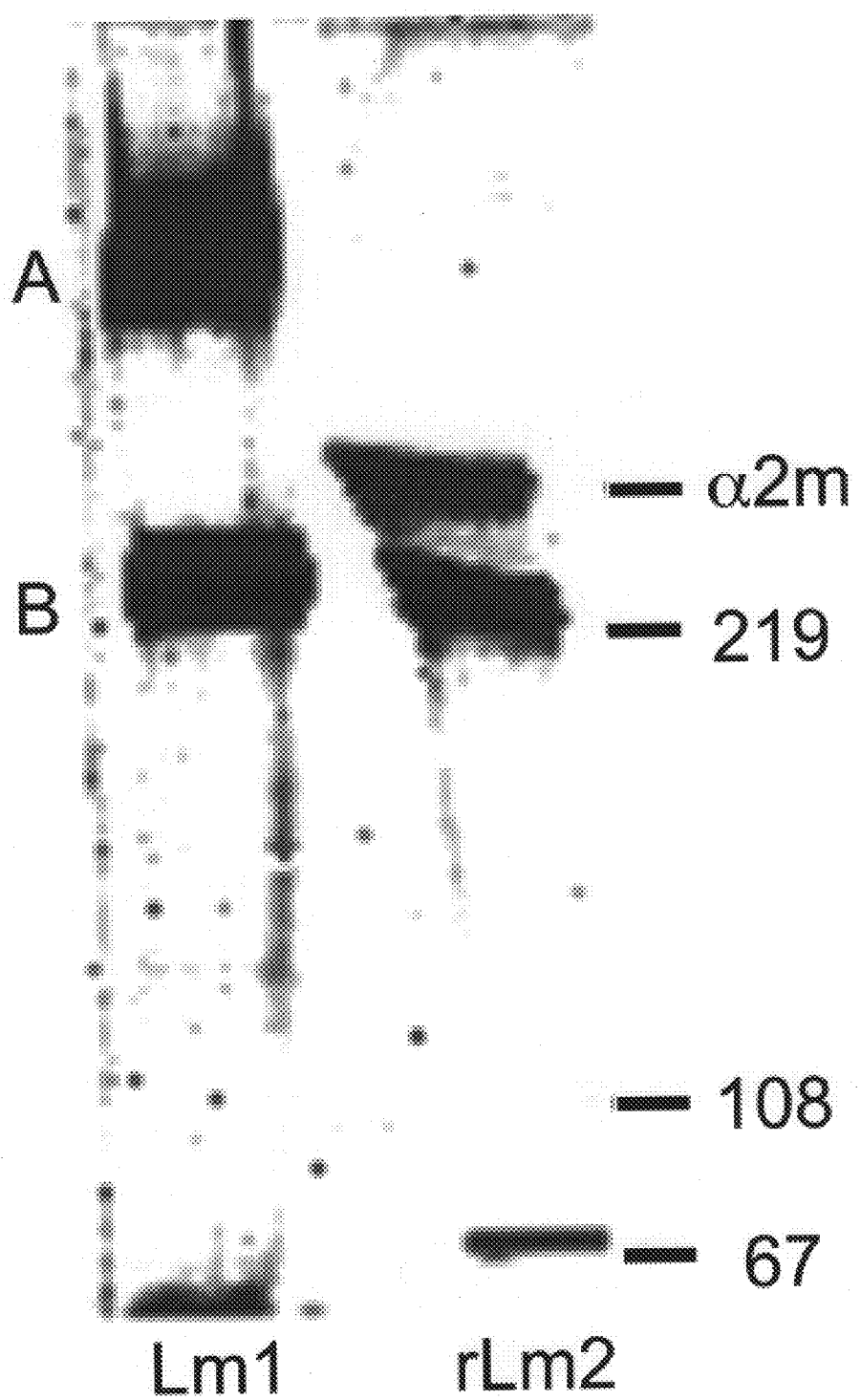
FIGS. 1A & 1B are a photograph of an Coomassie blue-stained SDS-polyacrylamide gel of recombinant laminin 2 compared to laminin 1.

All references, patents and patent applications are hereby incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer* and *Expression Protocols*, pp. 109–128, ed. E. J. Murray, The Humana Press Inc., Clifton, N.J.), and the Ambion 1998 Catalog (Ambion, Austin, Tex.).

As used herein, "laminin 2" includes both r-laminin 2 and laminin 2 substantially purified from tissue sources.

As used herein, the term "r-laminin 2" refers to recombinant laminin 2, expressed by a cell that has been transfected with one or more expression vectors comprising at least one nucleic acid sequence encoding a laminin 2 chain selected from the α2, β1 and γ1 chains, processed forms thereof, or other portions thereof that are capable of forming a heterotrimeric laminin 2 and maintaining laminin 2 activity. Such r-laminin 2 can thus comprise α2, β1, and γ1 sequences from a single organism, or from different organisms. Laminin 2 chain DNA sequences and their encoded proteins from a variety of organisms are known in the art. (See, for example, Vuolteenaho et al., J. Biol. Chem. 265:15611–15616 (1990); Kallunki et al., J. Biol. Chem. 266:221–228 (1991); Pikkarainen et al., J. Biol. Chem. 263:6751–6758 (1988); Sasaki and Yamada, J. Biol. Chem. 262:17111–17117 (1987); Sasaki et al., Proc. Natl. Acad. Sci. 84:935–939 (1987); Pikkarainen et al., J. Biol. Chem. 262:10454–10462 (1987); and Bernier et al., Matrix Biol. 14:447–455 (1995), all references incorporated by reference herein in their entirety).

The invention encompasses those laminin molecules wherein one or two of the chains that make up the recombinant heterotrimeric laminin 2 are encoded by endogenous laminin 2 chains. In a preferred embodiment, r-laminin 2 is produced by cells that are transfected with one or more expression vectors comprising nucleic acid sequences encoding each of mammalian α2, β1 and γ1 chains, processed forms thereof, or other portions thereof that are capable of forming a heterotrimeric laminin 2 and maintaining laminin 2 activity.

In the present invention, laminin 2 is a secreted protein, which is capable of being directed to the ER, secretory vesicles, and the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Such processing event can be variable, and thus may yield different versions of the final "mature protein". The substantially purified laminin 2 of the present invention includes heterotrimers comprising both the full length and any such processed laminin 2 chains.

As used herein, the term "substantially purified" means that the laminin 2 so designated has been separated from its in vivo cellular environment.

As used herein, a laminin 2 polypeptide chain refers to a polypeptide chain according to one or more of the following:
(a) comprises a polypeptide structure selected from the group consisting of:
1. R1-R2-R3
2. R1-R2-R3(e)
3. R3
4. R3(e)
5. R1-R3
6. R1-R3(e)
7. R2-R3
8. R2-R3(e)

wherein R1 is a amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from α2, β1, and γ1 chains; and R3(e) is a secreted laminin chain selected from the α2, β1, and γ1 chains that further comprises an epitope tag (such as those described below), which can be placed at any position within the laminin chain amino acid sequence; and/or (b) is encoded by a polynucleotide that is substantially similar to on or more of the disclosed laminin chain polynucleotide sequences (SEQ ID NOS.: 1, 3, 5, 7, 9, 11, 13, 15, 17, 19, 21, 23, 25, 27, 29, 31) or fragments thereof; and/or (c) is encoded by a polynucleotide that hybridizes under high or low stringency conditions to coding regions, or portions thereof, of one or more of the recombinant laminin 2 chain DNA sequences disclosed herein (SEQ ID NOS.: 1, 3, 5, 7, 9, 11, 13, 15, 17, 19, 21, 23, 25, 27, 29, 31) fragments thereof, or complementary sequences thereof; and/or (d) has at least 70% identity to one or more of the disclosed laminin 2 polypeptide chain amino acid sequences (SEQ ID NOS.: 2, 4, 6, 8, 10, 12, 14, 16, 18, 20, 22, 24, 26, 28, 30, 32, or fragments thereof), preferably at least 80% identity, and most preferably at least about 90% identity.

The phrase "substantially similar" is used herein in reference to polynucleotide or polypeptide sequences having one or more conservative variations from the laminin 2 sequences disclosed herein, including but not limited to deletions, insertions, inversions, repeats, and substitutions, wherein the resulting laminin chain is functionally equivalent to those disclosed herein.

For example, conservative polynucleotide variants may contain alterations in the coding regions, non-coding regions, or both. Especially preferred are polynucleotide variants containing alterations which produce silent substitutions, additions, or deletions, but do not alter the amino acid sequence of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, including but not limited to optimizing codon expression for a particular host (change codons in the human mRNA to those preferred by a bacterial host such as E. coli).

Naturally occurring conservative variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring conservative variants may be produced by mutagenesis techniques or by direct synthesis.

Using known methods of protein engineering and recombinant DNA technology, conservative polynucleotide variants may be generated to improve or alter the characteristics of the expressed laminin chain polypeptides. For instance, one or more amino acids can be deleted from the N-terminus or C-terminus of the secreted protein. (See, for example, Ron et al., J. Biol. Chem. 268: 2984–2988 (1993); Dobeli et al., J. Biotechnology 7:199–216 (1988)) Ample evidence demonstrates that variants often retain a biological activity similar to that of the naturally occurring protein. (See, for example, Gayleet al., J. Biol. Chem 268:22105–22111 (1993)). Furthermore, even if deleting one or more amino acids from the N-terminus or C-terminus of a polypeptide results in modification or loss of one or more biological functions, other biological activities may still be retained.

Guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and lie; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, "substantially similar" polypeptides of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be "substantially similar" according to the present invention.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

"Stringency of hybridization" is used herein to refer to conditions under which nucleic acid hybrids are stable. The invention also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are laminin 2-encoding nucleic acid sequences that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12, to obtain nucleotide sequences homologous to the nucleic acid molecules of the invention. BLAST protein searches are performed with the XBLAST program, score=50, wordlength=3, to obtain an amino acid sequence homologus to a polypeptide of the invention. To obtain gapped alignments for comparison purposes, Gapped BLAST is utilized as described in Altschul et al. (Nucleic Acids. Res. 25:3389–3402, 1997). When utilizing BLAST and Gapped BLAST programs, the default paramaters of the respective programs (e.g., XBLAST and NBLAST) are used. See the web site ncbi.nlm.nih.gov.

Further embodiments of the present invention include polynucleotides encoding laminin 2 chain polypeptides having at least 70% identity, preferably at least 80% identity, and most preferably at least 90% identity to one or more polypeptide sequence contained in SEQ ID NO:2, 4, 6, 8, 10, 12, 14, 16, 18, 20, 22, 24, 26, 28, 30, 32, or fragments thereof.

As used herein, "α2 polynucleotide" refers to a polynucleotide encoding an α2 laminin chain of the same name. Such polynucleotides can be characterized by one or more of the following: (a) the nucleotides of said polynucleotide may encode an amino acid sequence substantially similar to one or more of the amino acid sequences set forth in SEQ ID NO: 2, 4, 6, 8, 10, 12 or fragments thereof; (b) polynucleotides that encode polypeptides which share at least 70% identity, preferably 80% identity, and most preferably at least 90% identity with one or more of the sequences set forth in SEQ ID NO: 2, 4, 6, 8, 10, 12, or fragments thereof; (c) the α2 polynucleotides hybridize under low or high stringency conditions to the coding sequence set forth in one or more of SEQ ID NO: 1, 3, 5, 7, 9, 11, fragments thereof, or complementary sequences thereof; or (d) the α2 polynucleotides may encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted α2 chain polypeptides.

As used herein, "β1 polynucleotide" refers to polynucleotides encoding a β1 laminin chain of the same name. Such polynucleotides can be characterized by one or more of the following: (a) the nucleotides of said polynucleotide may encode a polypeptide substantially similar to one or more of the amino acid sequences set forth in SEQ ID NO: 14, 16, 18, 20, or fragments thereof; (b) polynucleotides that encode polypeptides which share at least 70% identity, preferably at least 80%, and most preferably at least 90% identity with one or more of the sequences set forth in SEQ ID NO: 14, 16, 18, 20, or fragments thereof; (c) the β1 cDNAs hybridize under low or high stringency conditions to the coding sequence set forth in one or more of SEQ ID NO: 13, 15, 17, 19, fragments thereof, or complementary sequences thereof; or (d) the β1 polynucleotides may encode a polypeptide with a general structure selected from (1) R1-R2-R3; (2) R1-R2-R3(e); (3) R3; (4) R3(e); (5) R1-R3;(6) R-1-R3(e); (7) R2-R3; and (8) R2-R3(e); wherein R1 and R2 are as described above, and R3 and R3(e) are as described above but comprise secreted β1 chain polypeptides.

As used herein, "γ1 polynucleotide" refers to polynucleotides encoding a γ1 laminin chain of the same name. Such polynucleotides can be characterized by one or more of the following: (a) the nucleotides of said polynucleotide may encode an amino acid that is substantially similar to one or more of the sequences set forth in SEQ ID NO: 22, 24, 26, 28, 30, 32, or fragments thereof; (b) polynucleotides that encode polypeptides which share at least 70% identity, preferably at least 80%, and most preferably at least 90% identity with one or more of the sequences set forth in SEQ ID NO: 22, 24, 26, 28, 30, 32, or fragments thereof; (c) the γ1 polynucleotides hybridize under low or high stringency conditions to the coding sequence set forth in one or more of SEQ ID NO: 21, 23, 25, 27, 29, 31, fragments thereof, or complementary sequences thereof; or (d) the γ1 polynucleotides may encode a polypeptide with a general structure selected from (1) R1-R2-R3; (2) R1-R2-R3(e); (3) R3; (4) R3(e); (5) R1-R3; (6) R1-R3(e); (7) R2-R3; and (8) R2-R3(e); wherein R1 and R2 are as described above, and R3 and R3(e) are as described above but comprise secreted γ1 chain polypeptides.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

As used herein, the term "increased biocompatibility" refers to reduced induction of acute or chronic inflammatory response, and reduced disruption of the proper differentiation of implant-surrounding tissues for laminin 2-coated biomaterials relative to an analogous, non-coated biomaterial.

In one aspect, the present invention provides r-laminin 2 expressing-cells that have been transfected with an expression vector containing promoter sequences that are operatively linked to nucleic acid sequences encoding at least one polypeptide sequence comprising the α2, β1 and γ1 chains of laminin 2, or fragments thereof, wherein the transfected cells secrete heterotrimeric laminin 2 containing the recombinant laminin chain. In a preferred embodiment, the cells are transfected with recombinant expression vectors containing promoter sequences that are operatively linked to nucleic acid sequences encoding polypeptide sequences comprising each of tile mammalian α2, β1 and γ1 chains of laminin 2, or fragments thereof. After the transfection(s), the cells express each of the recombinant laminin 2 chains, which form the heterotrimer, before r-laminin 2 secretion into the media.

In a preferred embodiment, cDNAs encoding α2, β1 and γ1 laminin chains, or fragments thereof, are subcloned into an expression vector. Alternatively, laminin 2 α2, β1 and/or γ1 genomic sequences, including one or more introns, can be used.

Any cell capable of expressing and secreting the r-laminin 2 can be used. Preferably, eukaryotic cells are used, and most preferably mammalian cells are used, including but not limited to kidney and epithelial cell lines. In a most preferred embodiment, the mammalian cells do not express all of the laminin 2 chains endogenously. Carbohydrate and disulfide post-translational modifications are believed to be required for laminin 2 protein folding and function. This makes the use of eukaryotic cells preferable for producing functional r-laminin 2, although other systems are useful for obtaining, for example, antigens for antibody production.

"Recombinant expression vector" includes vectors that operatively link a nucleic acid coding region or gene to any promoter capable of effecting expression of the gene product. The promoter sequence used to drive expression of the individual chains or r-laminin 2 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viruses.

In one embodiment, at least one of the laminin chain polynucleotide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin 2, so long as the resulting r-laminin 2 remains functional. Any epitope tag may be utilized, so long as it can be used as the basis for affinity purification of the resulting r-laminin 2. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals).

In another embodiment, one of the r-laminin 2 chains is expressed as a fusion protein with a first epitope tag, and at least one other r-laminin chain is expressed as a fusion protein with a second epitope tag. This simplifies the purification procedure and facilitates higher recoveries, Alternatively, the same epitope tag can be used to create fusion proteins with more than one of the r-laminin chains.

In a further embodiment, the epitope tag can be engineered to be cleaveable from the r-laminin 2 chain(s). Alternatively, no epitope tag is fused to any of the r-laminin 2 chains, and the r-laminin 2 is purified by standard techniques, including but not limited to affinity chromatography using antibodies against laminin 2 antibodies or other laminin 2 binding molecules.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In a preferred embodiment, the cells are stably transfected. Methods for stable transfection and selection of appropriate transfected cells are known in the art. In a most preferred embodiment, a CMV promoter driven expression vector is used in a human kidney embryonic 293 cell line.

In one example, media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin 2 secretion and/or activity, by any appropriate method, including Western blot analysis and cell binding assays. Activity of the r-laminin 2 is preferably analyzed in cell adhesion and protein binding assays.

In another aspect, the present invention provides substantially purified laminin 2, preferably r-laminin 2. In one embodiment, the substantially purified laminin 2 comprises a first chain comprising an α2 chain polypeptide; a second chain comprising a β1 chain polypeptide; and a third chain comprising a γ1 chain polypeptide. Alternatively, the r-laminin 2 comprises a first chain that is substantially similar to at least one of the sequences shown in SEQ ID NO: 2, 4, 6, 8, 10, 12 or fragments thereof; a second chain that is substantially similar to at least one of the sequence shown in SEQ ID NO: 12, 14, 16, or 18, or fragments thereof; and a third chain that is substantially similar to the sequence shown in SEQ ID NO: 20, 22, 24, or 26, or fragments thereof.

In another embodiment, the substantially purified r-laminin 2 comprises a first chain comprising a polypeptide that is at least about 70% identical to at least one of the sequences shown in SEQ ID NO: 2, 4, 6, 8, or 10, or fragments thereof; a second chain comprising a polypeptide that is at least 70% identical to at least one of the sequences shown in SEQ ID NO: 14, 16, 18, 20, or fragments thereof; and a third chain comprising a polypeptide that is at least 70% identical to at least one of the sequences shown in SEQ ID NO: 22, 24, 26, 28, 30, 32, or fragments thereof, wherein the first, second, and third polypeptides assemble into a recombinant heterotrimeric laminin 2.

It is preferred that at least one of the first, second, or third chains of the substantially purified human r-laminin 2 is expressed as a fusion protein with an epitope tag.

Alternatively, the r-laminin 2 comprises a heterotrimeric polypeptide structure, wherein each individual chain comprises a general structure selected from the group consisting of: (1) R1-R2-R3; (2) R1-R2-R3(e); (3) R3; (4) R3(e); (5) R1-R3; (6) R1-R3(e); (7) R2-R3; and (8) R2-R3(e)

wherein R1 is a amino terminal methionine; R2 is a signal sequence that is capable of directing secretion of the polypeptide, wherein the signal sequence may be the natural signal sequence for the particular laminin chain, that of another secreted protein, or it may be an artificial sequence; R3 is a secreted α2, β1, or γ1 laminin chain; and R3(e) is a secreted laminin α2, β1, and γ1 chain that further comprises an epitope tag (such as those described above), which can be placed at any position within the laminin chain amino acid sequence.

In a preferred embodiment, purification of the r-laminin 2 is accomplished by passing media from the transfected cells through an affinity column. For example, antibodies or other binding molecules that bind to a peptide epitope expressed on at least one of the recombinant chains are attached to an affinity column, and bind r-laminin 2 that has been secreted into the media. The r-laminin 2 is removed from the column by passing excess peptide through the column. The eluted protein can subsequently be further purified, if desired.

Eluted fractions are analyzed by any appropriate method, including gel electrophoresis and Western blot analysis. In a further embodiment, the peptide epitope can be cleaved after purification. In other embodiments, two or three separate r-laminin chains are expressed as fusion proteins, each with a different epitope tag, permitting two or three rounds of purification and a doubly or triply purified r-laminin 2. The epitope tag can be engineered so as to be cleavable from the r-laminin 2 chain(s) after purification. Alternatively, no epitope tag is fused to any of the r-laminin 2 chains, and the r-laminin 2 is purified by standard techniques, including but not limited to affinity chromatography using laminin 2 specific antibodies or other laminin 2 binding molecules.

In another aspect, the present invention provides a novel polynucleotide encoding the laminin α2 chain, consisting of the sequence shown in SEQ ID NO: 1. In another aspect, the present invention provides a novel laminin 2α polypeptide chain, consisting of the sequence shown in SEQ ID NO:2. These sequences differ from the previously reported sequences, in that the laminin α2-chain encoding nucleic acid consists of an extra nucleotide, resulting in the nucleic acid encoding an additional 30 amino acids at the C-terminus over what has previously been reported.

The present invention further provides pharmaceutical compositions comprising substantially purified laminin 2, and a pharmaceutically acceptable carrier. In a preferred embodiment, the pharmaceutical composition comprises substantially purified r-laminin 2. According to this aspect of the invention, other agents can be included in the pharmaceutical compositions, depending on the condition being treated. The pharmaceutical composition may further comprise one or more other compounds, including but not limited to any of the collagens, other laminin types, fibronectin, vitronectin, cadherins, integrins, α-dystroglycan, entactinnidogen, α-dystroglycan, glycoproteins, proteoglycans, heparan sulfate proteoglycan, glycosaminoglycans, epidermal growth factor, vascular endothelial growth factor, fibroblast growth factor, or nerve growth factors, and peptide fragments thereof. In an alternative embodiment, the pharmaceutical compositions comprise the novel laminin α2 polypeptide chain of the invention together with a pharmaceutically acceptable carrier.

Pharmaceutical preparations comprising substantially purified laminin 2 can be prepared in any suitable form, and generally comprise the substantially purified laminin 2 in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. Suitable solutions for use in accordance with the invention are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present invention, one may refer to Remington's Pharmaceutical Sciences, 15th Ed., Mack Publishing Co., Easton, Pa. (1975).

In further aspect, the present invention provides methods and kits for peripheral nerve regeneration, treatment of degenerative muscle disorders, regulating angiogenesis, promoting cell attachment and migration, ex vivo cell therapy, improving the biocompatibility of medical devices, improving the "take" of grafts, and preparing improved cell culture devices and media, comprising providing an amount effective of the substantially purified laminin 2, or pharmaceutical compositions thereof for the desired outcome. In all of these methods, the use of r-laminin 2 is preferred.

As used herein, the term "grafts" refers to both natural and prosthetic grafts as well as implants.

The treatment of peripheral nerve injuries is a common surgical problem. Nerve injuries can result from trauma, chronic compression, ischemia, radiation, errors of therapy and other causes. The severe forms of injury, in which the nerve is partially or completely disrupted, are difficult or impossible to treat by existing therapies. The basal lamina plays a key role in providing a migration guide for regenerating axons and Schwann cells following such nerve injury. The prognosis for successful regeneration is significantly better if the basement membrane remains intact.

Recently, the feasibility of using basal lamina coated bio-materials as a workable graft was demonstrated in a rat model in two studies (Kauppila et al., Exp. Neurol. 123:181–191 (1993); Tong et al., Brain Res. 663:155–162). In the first study, a bovine tendon collagen I graft sheet was impregnated with partially purified, non-recombinant mouse laminin-1, with the cut ends of the rat sciatic nerve (8 mm removed) sutured to the ends of the rolled graft. Function to the affected limb, as judged by electrophysiological and behavioral measurements at 4 months post-operatively, was restored (~60–80% relative to unaffected contralateral nerve) with the laminin graft at a level equivalent to restoring the transected nerve segment. The authors further reported that the laminin graft caused fewer signs of pain. In the second study, the authors created a graft by coating collagen fibrils with purified, non-recombinant laminin and fibronectin, and inserting the modified fibrils in a collagen sleeve. This graft, about 1 cm in length, was again sutured to the proximal and distal end of a transected sciatic nerve. Axonal/Schwann cell growth occurred into the graft with ultimate reattachment with the distal nerve stump. By light and electron microscopy, restoration of essential structural/cellular elements was found in the graft with ultimate resorption of the graft material. The laminin/fibronectin coat was essential since the collagen fibrils alone were not sufficient to restore the nerve.

The studies of Kauppila et al. and Tong et al. not only demonstrate the value of basal lamina components in regeneration, but also demonstrate therapeutic feasibility. A similar method for enhancing nerve regeneration using a hollow nerve regeneration conduit coated with type I collagen and purified placental laminin (predominately laminin 1) has also been disclosed. (U.S. Pat. No. 5,019,087)

Thus, in one embodiment, the present invention provides methods to promote peripheral nerve regeneration, comprising coating a nerve graft with an amount effective of substantially purified laminin 2, or pharmaceutical compositions thereof, to promote regeneration of the nerve. Laminin 2 is the predominant laminin isoform present in the endoneurial basement membrane of developing and mature peripheral nerves, and was shown to promote neuronal cell migration and regeneration, axon outgrowth, myelin membrane formation by oligodendrocytes, and Schwann cell migration. (Kamiguchi et al., (1998); Agius and Cochard, J. Neurosci. 18:328–338 (1998); U.S. Pat. No. 5,444,158; Buttery et al., Mol. Cell. Neurosci. 14:199–212 (1999); Bates and Meyer, Develop. Biol. 181:91–101 (1997)). The present invention provides a plentiful supply of substantially purified laminin 2, or pharmaceutical compositions thereof, for coating nerve grafts, and thereby promoting neuronal and Schwann cell migration, axonal migration, myelin membrane formation, and nerve regeneration. The graft can comprise a nerve graft, or a prosthetic graft. Both bioresorbable and non-resorbable materials have been used in tubes for bridging nerve gaps. (See for example, Nyilas, et al., (Trans. Soc. Biomater., 6, 85, 1983), Molander, et al. (Biomaterials, Vol. 4, pp. 276–280, October, 1983), Colin, et al., (Journal of Dental Research July, 1984, pp. 987–993).

In another embodiment, r-laminin 2 is used to promote the healing of degenerative muscle disorders. Laminin 2 is known to be important for myotube survival and maintenance of phenotype. (Vachon et al., J. Cell Biol. 134:1483–1497 (1996)). In vitro studies have demonstrated that partially purified laminin 2 promotes myoblast fusion and myotube formation. (Vachon et al., J. Cell Biol. 134:1483–1497 (1996)) In vivo experiments have shown partial laminin α2 chain restoration in a laminin α2 deficient, CMD animal model by primary muscle cell transplantation. (Vilquin et al., J. Cell Biol. 133:185–197 (1996)) Thus, mammalian cells that express r-laminin 2, or the novel laminin a2 chain of the invention, can be used for cell therapy, to treat patients with degenerative muscle disorders such as muscular dystrophies that are characterized by a laminin a2 deficiency.

Partially purified laminin 2 has also been shown to promote the migration of and attachment to a substrate of a variety of cell types, particularly muscle cells and cells of neuronal or mesenchymal origin. (U.S. Pat. No. 5,444,158; White et al., Am. J. Resp. Biol. 20:787–796 (1999); Engvall et al., Exp. Cell Res. 198:115–123 (1992))

Thus, in another embodiment, substantially purified laminin 2, or pharmaceutical compositions thereof, can be added to medical devices, tissue culture plates, grafts, and cell culture media to provide important ligand substrates to maintain and expand primary explanted human tissue cells. This takes advantage of what has been observed by many investigators over the past decade, i.e., basal lamina components, in particular laminins, provide optimal surfaces for the adhesion, spreading, propagation, and maintenance of the differentiated phenotype of a large variety of cells. This property of substantially purified laminin 2 can be exploited to increase the biocompatibility of a medical device, to permit the maintenance of human cells in a laboratory affording time to find a suitable donor, and for the expansion of cell populations for transplantation and somatic gene therapy. Possible target cells for ex vivo therapy include cells of muscle and neuronal origin, lymphocytes and cells of the immune system, pancreatic islet, parathyroid, adrenal, pituitary, hepatic, cardiac muscle and stem cells.

In another embodiment, the present invention provides methods for regenerating cells and tissues both in vivo and ex vivo. Many of the current approaches for tissue engineering begin with a collagen/polymer scaffolding that is seeded with appropriate cells that can proliferate and differentiate into cell masses and tissue sub-structures. In the development of these methods, attempts have been made to add coatings to the scaffolding to provide for a more natural surface for cell interactions, with the expectation that cell proliferation and tissue development would be enhanced. Coating these matrices with the substantially purified laminin 2 provides for a natural ligand interactive surface to promote normal cell adherence, cell growth and tissue development. Thus, the availability of substantially purified laminin 2 is expected to significantly improve tissue regeneration procedures.

Laminins, or cell extracts containing laminins, have been shown to regulate angiogenesis in a biphasic manner. (See, for example, Nicosia et al., Dev. Biol. 164:197–206 (1994); Bonfil et al., Int. J. Cancer 58:233–239 (1994)). At lower concentrations (30–300 µg/ml), a laminin-entactin complex stimulated angiogenesis in a three-dimensional culture, while at 3000 µg/ml the same complex was inhibitory to angiogenesis. Thus, in another aspect, the present invention provides methods for regulating angiogenesis, comprising contacting a tissue or culture substrate with an amount effective of laminin 2 or pharmaceutical compositions thereof to regulate angiogenesis. In one embodiment, the laminin 2 is used to promote angiogenesis by contacting a tissue or culture substrate with an amount effective of laminin 2 to promote angiogenesis. In another embodiment, the laminin 2 is used to inhibit angiogenesis, by contacting the tissue or culture substrate with an amount effective of laminin 2 to inhibit angiogenesis. An example of culture substrates to be contacted with laminin 2 to regulate angiogenesis are those used for tissue engineering purposes.

In a further aspect, the present invention comprises medical devices with improved biocompatibility, wherein the devices are coated with the substantially purified laminin 2, or pharmaceutical compositions thereof, alone or in combination with other proteins or agents that serve to increase the biocompatibility of the device surface. The coated device stimulates cell attachment and provides for diminished inflammation and/or infection at the site of entry of the appliance.

Preferably, the device is made of or coated with a biocompatible metal that may be either stainless steel or titanium. Alternatively, the device is made of or coated with a ceramic material, or a polymer including but not limited to polyester, polyglycolic acid or a polygalactose-polyglycolic acid copolymer.

One particular use of the present invention is to increase neuronal, skeletal muscle, endothelial or mesenchymal cell adhesion to target surfaces. For example, vascular grafts and stents may be coated with substantially purified laminin 2 to stimulate endothelial cell attachment, and to minimize platelet adhesion to the graft or stent surface. Alternatively, bone or connective tissue grafts or prostheses may be coated with substantially purified laminin 2 to stimulate adhesion of the appropriate cell type and improved efficiency of grafting.

If the device is made of a natural or synthetic biodegradable material in the form of a mesh, sheet or fabric, substantially purified laminin 2 may be applied directly to the surface thereof. Appropriate cells may then be cultured on the matrix to form transplantable or implantable devices, including dental abutment pieces, needles, metal pins or rods, indwelling catheters, colostomy tubes, surgical meshes and any other appliance for which coating with the substantially purified laminin 2 is desirable. Alternatively, the devices may be implanted and cells may be permitted to attach in vivo.

Coupling of the substantially purified laminin 2 may be non-covalent (such as by adsorption), or by covalent means. The device may be immersed in, incubated in, or sprayed with substantially purified laminin 2 or pharmaceutical compositions thereof. The dosage regimen for various treatments using the substantially purified laminin 2 of the present invention is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized. Laminins are sometimes present in an insoluble form in the basement membrane and have the capability of polymerizing at concentrations as low as about 50 µg/ml, depending on the laminin isoform and the conditions. Laminins can also polymerize into a gel at a concentration of 2–3 mg/ml. Dosage levels of the order of between 1 ng/ml and 10 mg/ml are thus useful for all methods disclosed herein, preferably between about 1 µg/ml and about 3 mg/ml.

The present invention also provides a method for inducing cell attachment to the device (as disclosed above), comprising coating the appliance with substantially purified laminin 2 prior to incubation with cells appropriate for the desired application.

In another aspect of the present invention, substantially purified laminin 2 is used for the culture of cells, including but not limited to neuronal, skeletal muscle, fibroblasts, Schwann cells, cells of mesenchymal origin, and endothelial cells, by contacting the cells with an amount effective of substantially purified laminin 2 to stimulate attachment and proliferation/differentiation/stasis of cells. The substantially purified laminin 2 can either be provided in the cell culture medium, or as a cell culture medium supplement, or may be coated on the surface of a cell growth substrate. In a preferred embodiment, the method further includes contacting the cells with other compounds, including but not limited to any of the collagens, other laminin types, fibronectin, vitronectin, cadherins, entactinnidogen, α-dystroglycan, glycoproteins, proteoglycans, heparan sulfate proteoglycan, glycosaminoglycans, epidermal growth factor or nerve growth factors, and peptide fragments thereof.

The cells may comprise primary cells or cell culture cell lines. The methods of this aspect of the invention can be used in vivo, ex vivo, or in vitro.

In a preferred embodiment, r-laminin 2 is used to coat the surface of a substrate, to promote cell adhesion to the substrate, and to stimulate cell proliferation/differentiation/stasis. The substrate used herein may be any desired substrate. For laboratory use, the substrate may be as simple as glass or plastic. For use in vivo, the substrate may be any biologically compatible material capable of supporting cell growth. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene and virtually any other material to which biological molecules can readily adhere.

In a further aspect, the present invention provides cell growth substrates for the adhesion and proliferation of cells in culture, by providing an amount effective of substantially purified laminin 2 for the attachment of cells to a cell culture device for the attachment and subsequent proliferation, differentiation, or stasis of the cells. The substrates may comprise any of the substrates discussed above. Preferably, r-laminin 2 is coated on the surface of the substrate at a concentration of between about 1 ng/ml and about 10 mg/ml, and more preferably 1 ng/ml and about 10 $\mu$g/ml.

In another aspect of the present invention, an improved cell culture medium is provided, wherein the improvement comprises addition to the cell culture medium of an effective amount of substantially purified laminin 2 to the cell culture medium to promote the adherence, proliferation, differentiation, or stasis of cells. Any cell culture media that can support the growth of cells can be used with the present invention. Such cell culture media include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, Opti-MEM® Reduced-Serum Medium, RPMI Medium, and Macrophage-SFM Medium or combinations thereof.

The improved cell culture medium can be supplied in either a concentrated (ie: 10×) or non-concentrated form, and may be supplied as either a liquid, a powder, or a lyophilizate. The cell culture may be either chemically defined, or may contain a serum supplement. Culture media is commercially available from many sources, such as GIBCO BRL (Gaithersburg, Md.) and Sigma (St. Louis, Mo.). In an alternative embodiment, the r-laminin 2 is used as a cell culture supplement.

The present invention may be better understood with reference to the accompanying examples that are intended for purposes of illustration only and should not be construed to limit the scope of the invention, as defined by the claims appended hereto.

EXAMPLES

Recombinant Laminin-2 cDNAs coding for the complete open reading frame of the human $\beta 1$ chain and the human $\gamma 1$ chain have been described. (Kallunki et al., J. Biol. Chem. 266:221–228 (1991); Pikkarainen et al., J. Biol. Chem. 262:10454–10462 (1987); Pikkarainen et al., J. Biol. Chem. 263:6751–6758 (1988); Pikkarainen et al., Eur. J. Biochem. 209:571–582 (1992)). The $\gamma 1$ cDNA was modified to contain a 3' end (corresponding to the C-terminal end) insertion coding for the FLAG peptide epitope tag (SEQ ID NO:25). The complete human laminin $\alpha 2$ cDNA was constructed from the large (approximately 2/3 of open reading frame) cDNA as described in (Vuolteenaho et al., J. Cell Biol. 124:381–394 (1994)) with the C-terminal (3'-end) cDNA as described in (Ehrig et al., Proc. Natl. Acad. Sci. 87:3264–3268 (1990)). The $\beta 1$, $\gamma 1$, and $\alpha 2$ cDNAs were inserted into the pCIS (Genentech, South San Francisco, Calif.), pRC-CMV, and pCEP4 (InVitrogen, Inc., Carlsbad, Calif.) mammalian expression vectors respectively. pRC-CMV contained a neo (G418) expression cassette and pCEP4 contained a puromycin expression cassette, each under a separate promoter. Transfection of human embryonic kidney 293 cells (adenovirus transformed, ATCC CRL 1573) with the $\gamma 1$-FLAG expression vector was carried out by calcium phosphate precipitation in 35 mm plastic dishes as previously described (Yurchenco et al., Proc. Natl. Acad. Sci. 94:10189–94 (1997)). Laminin $\gamma 1$ expressing stable clones were selected in the presence of G418 antibiotic. These cells were found to express the laminin $\gamma 1$ chain that reacted with both laminin and FLAG-specific antibodies in immunoblots. One such clone was subsequently co-transfected with the expression vector DNA coding for the $\alpha 2$ and $\beta 1$ laminin chains. New clones were selected in the presence of G418+puromycin. A clone (designated #44) was determined to express all three laminin 2 chains, by using polyclonal antibodies specific for placental laminin and the $\alpha 2$-G domain, $\beta 1$ chain, and FLAG epitope tag (Cheng et al., J. Biol. Chem. 272:31525–32 (1997); Rambukkana et al., Cell 88:811–821 (1997)). This clone was expanded in tissue culture. Conditioned serum-containing medium was collected and pooled for purification of secreted protein.

Purification of Recombinant Laminin 2

The procedure is described for 100 ml of pooled conditioned medium. Purification was carried out at 4°–10° C. in a cold room. A small column was packed with two ml of heparin-Sepharose-4B beads and equilibrated with Tris-buffer (50 mM Tris-HCl, pH 7.4, containing 1 MM EDTA and 0.1 mM PMSF) diluted 2:1 with water. The medium was passed through the column. The column was then washed with several volumes of Tris-buffer to decrease the NaCl concentration. One ml of anti-FLAG M2 agarose affinity gel suspension (Sigma-Aldrich, St. Louis, Mo.) was added to the preparation and used to absorb the recombinant protein bearing the FLAG epitope tag. After washing five times with Tris-buffer, 0.1 mg (in one ml) of FLAG peptides (Sigma-Aldrich) was added to elute the recombinant laminin protein from the beads. The protein was freed of peptides with a spin column. Recombinant protein was characterized by SDS-polyacrylamide gel electrophoresis (SDS-PAGE) (FIG. 1), immunoblotting, and Pt/C rotary shadow electron microscopy (FIG. 2).

Recovered yields of recombinant laminin 2 were 6 $\mu$g/ml purified protein from conditioned medium (determined from a 100 ml batch preparation). The recombinant laminin had three Coomassie blue-staining bands, the larger corresponding to the $\alpha 2$ subunit. (FIG. 1) Some unprocessed (i.e.: uncleaved) $\alpha 2$ chain was typically observed. The cleaved version contained a high molecular weight band (approximately 300 kDa) and a 75 kDa band, the latter the predicted G fragment. (Cheng et al., J. Biol. Chem. 272:31525–32 (1997) The two forms of laminin 2 could be separated from each other by heparin affinity chromatography.

Figure 2:
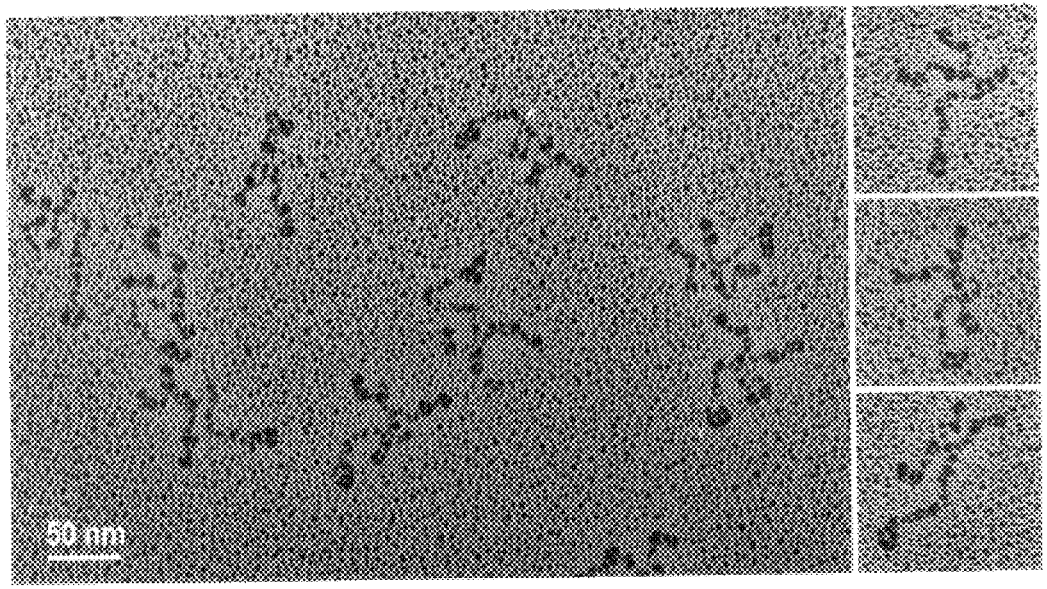
FIG. 2 is an electron micrographs of purified recombinant laminin 2.

FIG. 2 is an electron micrograph of purified r-laminin 2, which was dialyzed into 0.1 5M ammonium bicarbonate, mixed with glycerol to a final ratio of 6:4 glycerol:buffer, and nebulized onto freshly cleaved mica. The sample was evacuated in a Balzars BAF-500K freeze-etch unit and rotary shadowed at an 8° angle with 0.9 nm Pt/C as described (Yurchenco et al., Proc. Natl. Acad. Sci. 94:10189–94 (1997)). As can be seen from the figure, r-laminin 2 demonstrates the cruciform structure that is typical of endogenously expressed laminin molecules.

Functional Data

Figure 3:
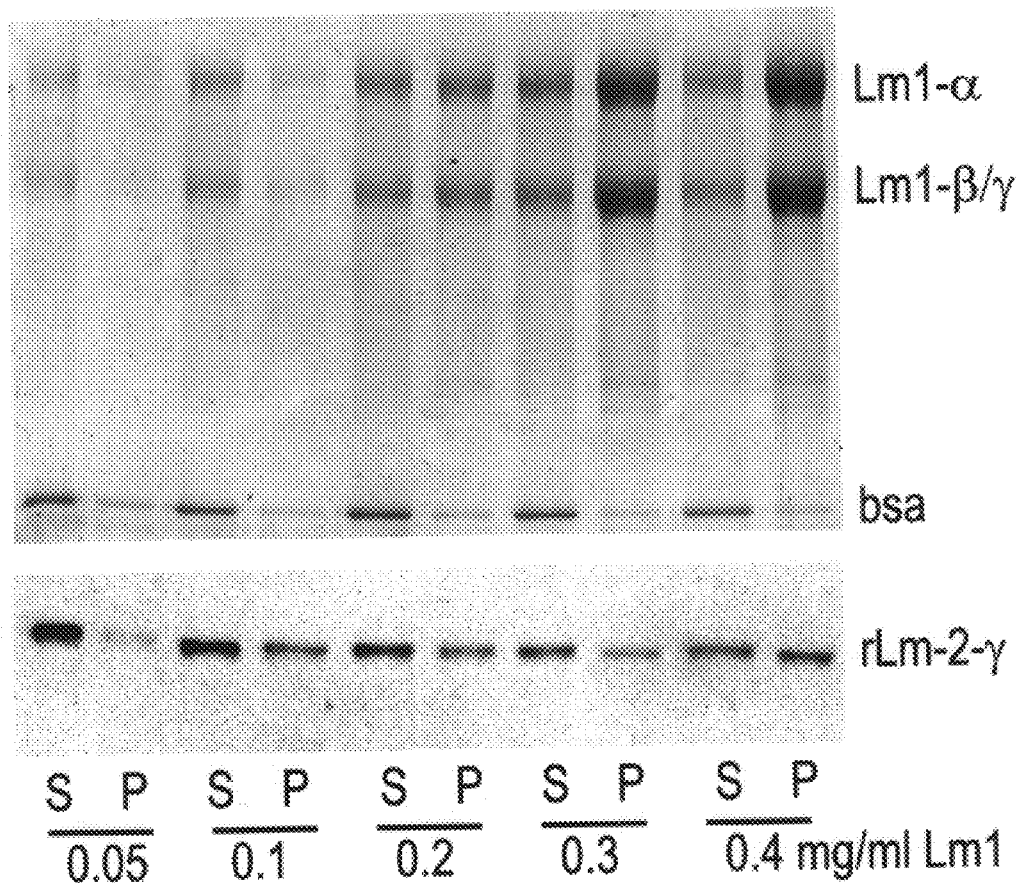
FIG. 3 is an immunoblot demonstrating the co-polymerization of laminin 2.

Recombinant laminin 2 was found to possess self-assembly activity in a co-polymerization assay (FIG. 3). A fixed trace amount of r-laminin 2 was mixed with increasing concentrations of laminin 1 in separate tubes (each containing a small amount of bovine serum albumin (BSA)) and incubated at 37 µC as described (Cheng et al., J. Biol. Chem. 272:31525–32 (1997)). The incubation mixtures were then centrifuged in supernatant (S) and polymer pellet (P) fractions. Laminin 2 was detected with FLAG-specific antibody. At higher conentrations, increasing fractions of laminin 2 are detected in the pellet fraction, evidence for laminin-type polymerization.

Figure 4:
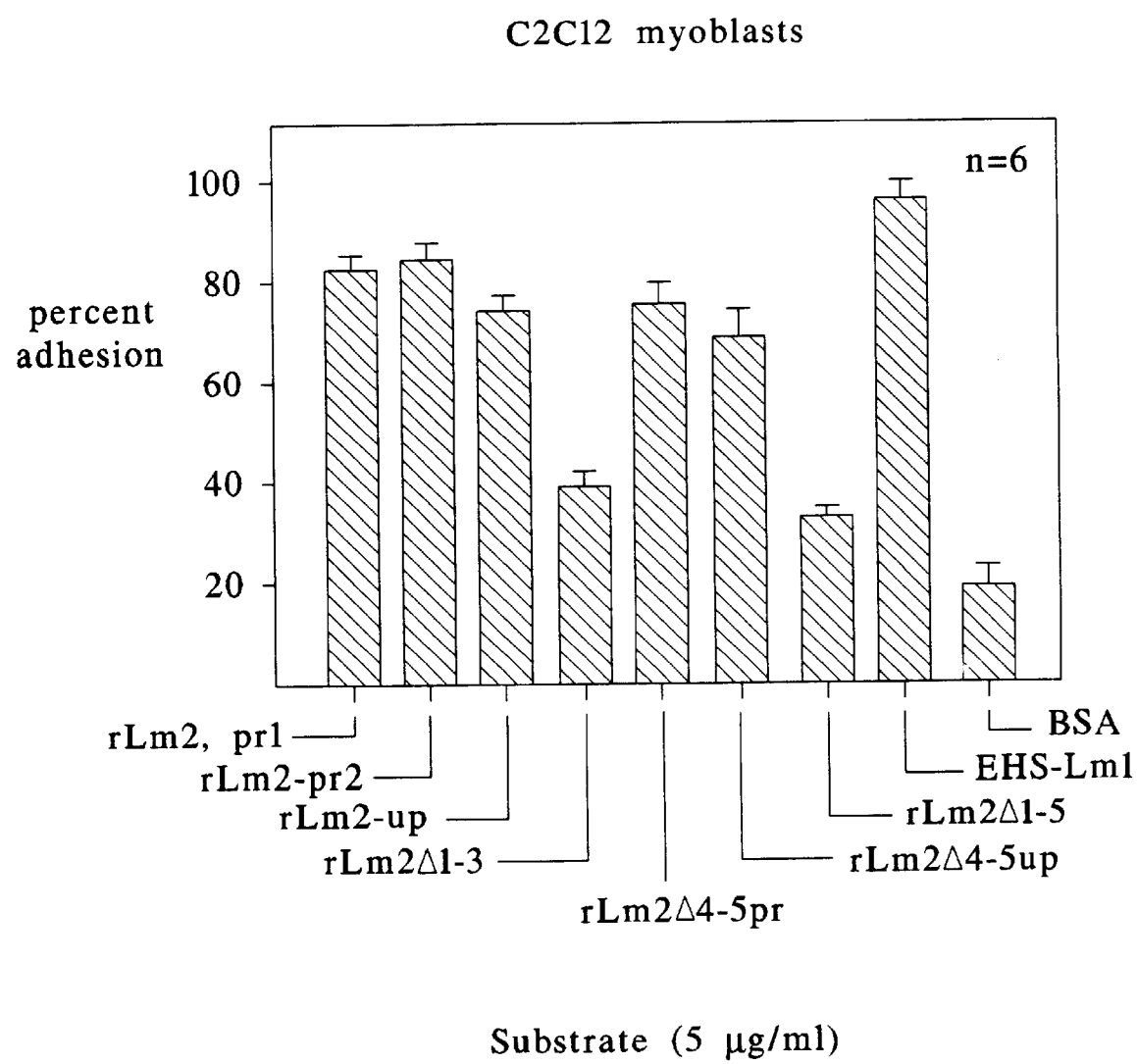
FIG. 4 is a graph demonstrating C2C12 myoblast adherence to recombinant laminin 2.

R-laminin 2 was also found to support adhesion and spreading of C2C12 myoblasts (FIG. 4), but not HT1080 fibrosarcoma cells (data not shown). Cultured myoblasts were added to 96-well culture dishes previously coated with two preparations of r-laminin 2 (two left bars), or with r-laminin 2 bearing different deletions of the G domain, all at 5 4g/ml. Deletion of G1–3 sub-domains (which bears the α7β1 integrin binding site), or all of G (which also removes the dystroglycan sites) greatly reduced binding.

Human Laminin α2 Polynucleotide and Polypeptide

We have determined that the published sequence of the human laminin α2 nucleic acid and protein sequences (Ehrig et al., PNAS 87:3264–3268 (1990) are incorrect. An erroneous dropped G base that should lie near the 3' end of the nucleic acid sequence (FIG. 5), leads to a prediction of a prematurely truncated laminin alpha2-G domain. The correct amino acid sequence for the α2 chain protein is shown in FIG. 5.

One of the most serious consequences of the erroneous sequence may be that the end of the G domain is predicted to lack a cysteine residue that is conserved in different laminins, and is present in the corrected sequence presented here. It is thought that this cysteine pairs with another cysteine in the G domain and is important for protein conformation. Furthermore, if the incorrect sequence is used, an epitope tag placed at the apparent C-terminus will in fact be out of frame, and thus the epitope tag will not be functional.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6632790B1). An electronic copy of the "Sequence Listing" will also be available from the USPTO upon request and payment of the fee set forth in 37 CFR 1.19(b)(3).

I claim:

1. A substantially purified laminin α2 chain polypeptide comprising the amino acid sequence shown in SEQ ID NO:2, or a secreted form thereof.

2. Substantially purified laminin 2 comprising:
   (a) a laminin α2 chain polypeptide comprising the amino acid sequence shown in SEQ ID NO:2 or a secreted form thereof;
   (b) a laminin β1 chain polypeptide comprising an amino acid sequence that shares at least 70 percent identity to an amino acid sequence of one or more of SEQ ID NO:14, and 16, or a secreted form thereof; and
   (c) a laminin γ1 chain polypeptide comprising an amino acid sequence that shares at least 70 percent identity to an amino acid sequence of one or more of SEQ ID NO:22, 24, 26, and 28, or a secreted form thereof;
   wherein the substantially purified laminin 2 supports adhesion of C2C12 myoblasts.

3. The substantially purified laminin 2 of claim 2 wherein the laminin β1 chain polypeptide comprises an amino acid sequence that shares at least 80 percent identity to an amino acid sequence of one or more of SEQ ID NO:14, and 16, or a secreted form thereof; and the laminin γ1 chain polypeptide comprising an amino acid sequence that shares at least 80 percent identity to an amino acid sequence of one or more of SEQ ID NO:22, 24, 26, and 28, or a secreted form thereof.

4. The substantially purified laminin 2 of claim 2 wherein the laminin β1 chain polypeptide comprises an amino acid sequence that shares at least 90 percent identity to an amino acid sequence of one or more of SEQ ID NO:14, and 16, or a secreted form thereof; and the laminin γ1 chain polypeptide comprising an amino acid sequence that shares at least 90 percent identity to an amino acid sequence of one or more of SEQ ID NO:22, 24, 26, and 28, or a secreted form thereof.

5. The substantially purified laminin 2 of claim 2 wherein the laminin β1 chain polypeptide comprises an amino acid sequence selected from the group consisting of SEQ ID NO:14, and 16 or a secreted form thereof; and the laminin γ1 chain polypeptide comprises an amino acid sequence selected from the group consisting of SEQ ID NO:22, 24, 26, and 28 or a secreted form thereof.

6. The substantially purified laminin 2 of claim 2 wherein:
   the laminin β1 polypeptide chain is encoded by a polynucleotide that hybridizes under high stringency conditions to a coding region of one or more of SEQ ID NO:13, and 15; and the laminin γ1 polypeptide chain is encoded by a polynucleotide that hybridizes under high stringency conditions to a coding region of one or more of SEQ ID NO: 21, 23, 25, and 27;

wherein the laminin α2 polypeptide chain, the laminin β1 polypeptide chain, and the laminin γ1 polypeptide chain are assembled into recombinant heterotrimeric laminin 2, and wherein the high stringency conditions comprise overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 65° C.

7. The substantially purified laminin 2 of claim 2 wherein the laminin α2 polypeptide chain, the laminin β1 polypeptide chain, and the laminin γ1 polypeptide chain each comprise a general structure selected from the group consisting of: (1) R1-R2-R3; (2) R1-R2R-3(e); (3) R3; (4) R3(e); (5) R1-R3; (6) R1-R3(e); (7) R2-R3; and (8) R2-R3(e)

wherein R1 is an amino terminal methionine; R2 is a signal sequence that is capable of directing secretion of the polypeptide, wherein the signal sequence may be the natural signal sequence for the particular laminin chain, that of another secreted protein, or it may be an artificial sequence; R3 is a secreted α2 laminin chain for the laminin α2 polypeptide chain, a secreted β1 laminin chain for the laminin β1 polypeptide chain, and γ1 laminin chain for the laminin γ1 polypeptide chain; and R3(e) is identical to R3, but further comprises an epitope tag.

8. A pharmaceutical composition comprising:

a) the substantially purified laminin 2 of any one of claims 2–7; and b) a pharmaceutically acceptable carrier.

* * * * *